United States Patent [19]
Morris

[11] 4,260,766
[45] Apr. 7, 1981

[54] PREPARATION OF (DICHLOROMETHYL) PYRIDINES BY REDUCTIVE DECHLORINATION

[75] Inventor: Leo R. Morris, Midland, Mich.

[73] Assignee: The Dow Chemical Company, Midland, Mich.

[21] Appl. No.: 100,084

[22] Filed: Dec. 4, 1979

[51] Int. Cl.³ .................. C07D 213/26; C07D 213/55; C07D 213/57
[52] U.S. Cl. .................................... 546/303; 546/286; 546/287; 546/298; 546/299; 546/301; 546/302; 546/345; 546/346
[58] Field of Search ............... 546/345, 346, 286, 301, 546/302, 287, 298, 299, 303

[56] References Cited
U.S. PATENT DOCUMENTS

| | | | |
|---|---|---|---|
| 3,420,833 | 1/1969 | Taplin | 546/180 |
| 3,591,596 | 7/1971 | Wang et al. | 546/294 |
| 4,062,962 | 12/1977 | Noveroske | 424/263 |
| 4,143,144 | 3/1979 | Tobol et al. | 424/263 |

Primary Examiner—Alan L. Rotman
Attorney, Agent, or Firm—S. Preston Jones; Ronald G. Brookens

[57] ABSTRACT (Dichloromethyl) substituted pyridines are prepared from (trichloromethyl) substituted pyridines by the reaction thereof under reductive dechlorination conditions with metallic iron or a ferrous iron compound and an acid.

6 Claims, No Drawings

PREPARATION OF (DICHLOROMETHYL) PYRIDINES BY REDUCTIVE DECHLORINATION

BACKGROUND OF THE INVENTION (Dichloromethyl) substituted pyridines are known compounds which find utility as pesticides for the control of plant, insect and fungal pests, among others, and as intermediates for preparing compounds having the above utilities. Representative patents which teach such uses include U.S. Pat. Nos. 3,420,833; 3,591,596; 4,062,962 and 4,143,144.

(Dichloromethyl) substituted pyridines have been prepared from (trichloromethyl) substituted pyridines by a variety of procedures. A few of these procedures include, for example, dehydrochlorination over a palladium catalyst in the presence of formic acid, electrolytic reduction, reductions employing either zinc or stannous chloride with hydrochloric acid and the like. The prior processes, while producing the desired product, have not found wide success because of one or more shortcomings such as expense of reagents, slow reaction rate, poor selectivity to the desired product or the difficulty in treating waste streams for recycle and/or disposal.

SUMMARY OF THE INVENTION

The present invention is directed to a process for preparing (dichloromethyl) substituted pyridines corresponding to the formula

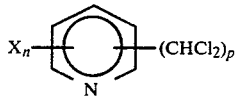

wherein X represents chloro, bromo, fluoro, aryloxy, alkoxy of 1 to 4 carbon atoms, alkenyloxy of 2 of 4 carbon atoms, cyano, alkyl of 1 to 4 carbon atoms or carboxy; n represents an integer of from 0 to 4 and p is 1 or 2.

In carrying out the process of the present invention, a (trichloromethyl) substituted pyridine corresponding to the formula

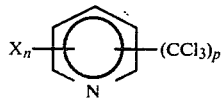

wherein X n and p are as hereinbefore set forth, is reacted, under reductive dechlorination conditions, with metallic iron or a ferrous iron compound and an acid.

In the present specification and claims, the term "aryloxy" is employed to designate phenoxy and substituted phenoxy wherein the substituent can be independently one or two $C_1$–$C_4$ alkyl, $C_1$–$C_4$ alkoxy, $C_1$–$C_4$ alkylthio, $C_1$–$C_4$ alkylsulfonyl, trifluoromethyl, chloro, bromo or fluoro groups.

Representative ferrous iron compounds useful in carrying out the present invention include ferrous chloride and ferrous sulfate. It is preferred to use ferrous chloride or metallic iron.

Solvents which can be employed in the practice of the present invention include, for example, acetone and the lower alkanols ($C_1$–$C_4$) or mixtures thereof. While the reaction can be carried out in the absence of a solvent, it is preferable that one be used.

The acid employed in the practice of the present invention can be organic or inorganic. Preferred acids include hydrochloric acid or acetic acid and mixtures of the acids can also be employed.

Representative (trichloromethyl) pyridines which can be employed in the practice of the present invention include among others
2-chloro-6-(trichloromethyl)pyridine,
2-chloro-4-methoxy-6-(trichloromethyl)pyridine,
2-chloro-6-methoxy-4-(trichloromethyl)pyridine,
2-chloro-6-ethoxy-4-(trichloromethyl)pyridine,
2-chloro-6-phenoxy-4-(trichloromethyl)pyridine,
3,5-dichloro-6-(trichloromethyl)pyridine,
2-chloro-4,6-di(trichloromethyl)pyridine,
2-phenoxy-6-(trichloromethyl)pyridine,
2-(4-chlorophenoxy)-6-(trichloromethyl)pyridine,
2-(3-fluorophenoxy)-6-(trichloromethyl)pyridine,
2-(4-fluorophenoxy)-6-(trichloromethyl)pyridine, and
2-(4-methoxyphenoxy)-6-(trichloromethyl)pyridine.

The reaction is initiated by contacting the reactants together in any order. They may all be mixed together and then heated together or the pyridine compound, solvent and metallic iron or ferrous iron compound mixed together and the acid added slowly thereto.

The reaction is conveniently carried out at the reflux temperature of the mixture. Depending upon the reactants, this can be between ~80° and ~120° C. Temperatures below about 75° C. are not usually employed since the reaction rate at these temperatures is reduced and such reduced reaction rates are not practical. Temperatures above reflux, i.e. carried out at higher than atmospheric temperature, offer little or no advantage and only increase the cost of the operation.

The molar equivalent of the metallic iron or iron compound to the pyridine reactant varies depending on whether metallic iron or a ferrous iron compound is employed and whether there is one or two trichloromethyl groups on the pyridine reactant. The molar equivalent is usually between ~0.50 and ~3.0 moles of the metallic iron or ferrous iron compound per trichloromethyl group on the pyridine compound. In the case of metallic iron, an optimum molar equivalent of ~0.50 to ~1.0 mole of iron per trichloromethyl group on the pyridine compound is employed. With ferrous chloride or sulfate, an optimum molar equivalent of from ~1.0 to ~3.0 moles of the ferrous iron compound per trichloromethyl group on the pyridine compound has been found to be useful. The use of amounts less than the optimum amount leads to incomplete reduction, while an amount in excess of the above gives over reduction, i.e. formation of monochloromethyl or further reduction to the methyl group itself.

After the completion of the reaction, the reaction product is cooled and extracted throughly with a solvent such as chloroform, methylene chloride, toluene or tetrachloroethylene. Additionally, the reaction mixture is washed with water or dilute hydrochloric acid and dried. The reaction mixture can also be filtered to remove any insolubles. The crude product can be employed as such without further treatment, or if desired, the product can be purified by recrystallization from a solvent such as heptane, methanol, aqueous acetone or by distillation under reduced pressure.

DESCRIPTION OF SOME PREFERRED EMBODIMENTS

In order that the process of the present invention can be more fully understood, the following examples are given to illustrate the manner by which the process can be practiced, but, as such, should not be construed as limitations upon the overall scope of the same.

EXAMPLE I:

Preparation of 2-chloro-6-(dichloromethyl)-pyridine

Into a 250 milliliter (ml) flask fitted with a condenser, magnetic stirrer and dropping funnel were added 46.2 grams (g) (0.20 mole) of 2-chloro-6(trichloromethyl)-pyridine, 30 g of methanol and 9.1 g (0.16 mole) of 20 mesh iron filings. The mixture was heated to 70° C. and 30 g of concentrated hydrochloric acid was added thereto over a 5 minute period. A slight exotherm occurred and the mixture was heated and maintained under reflux (83°–86° C.) for 1 hour. The reaction mixture was cooled to 45° C., and 50 ml of methylene chloride was added thereto. The mixture was filtered through diatomaceous earth and the filter cake washed thoroughly with water and then with methylene chloride. The filtrates were combined and the methylene chloride phase separated from the water phase. The product from a second run was combined with the above product mix and the mixture concentrated to a pot temperature of 95° C. at 15 millimeters of mercury (mm Hg). This residue was present in an amount of 74.5 g and melted at 48°–52° C. Analysis by gas-liquid chromatography (glc) showed a yield of 90.1 percent 2-chloro-6-(dichloromethyl)pyridine, 3.7 percent 2-chloro-6-(chloromethyl)pyridine and 1.7 percent 2-chloro-6-(trichloromethyl)pyridine. The 2-chloro-6-(dichloromethyl)pyridine was recovered by recrystallization from heptane and melted at 53.3°–54.0° C.

EXAMPLE II:

Preparation of 2-chloro-6-(dichloromethyl)pyridine

A mixture of 23.1 g (0.10 mole) of 2-chloro-6-(trichloromethyl)pyridine, 10.0 g of methanol, 15.0 g of concentrated hydrochloric acid and 40.0 g (0.20 mole) of ferrous chloride as the tetrahydrate was stirred while heating to reflux. The mixture was a slurry which slowly became fluid and a two-phase liquid mixture resulted after 15 minutes. The mixture was maintained under reflux conditions (80°–90° C.) for one and one-half hours and then cooled to ~45° C. The mixture was extracted with 50 ml of methylene chloride and then 20 ml of water. The extracts were combined and the organic phase separated. Further dilution of the aqueous phase with water and extraction with 20 ml of methylene chloride gave an oil which was combined with the main extract and washed once with water. The crude product mixture was recovered in a yield of 88 g and after drying over anhydrous sodium sulfate, analyzed by glc. This analysis showed the mix to contain 82 percent 2-chloro-6-(dichloromethyl)pyridine, 4 percent 2-chloro-6-(trichloromethyl)pyridine and ~14 percent unresolved impurities.

The combined product mixture of several runs carried out in a fashion similar to Example II was concentrated and distilled using a 10-plate Oldershaw column. A forecut containing the volatile impurities was separated and the main cut which boiled at 113° C. at 9 mmHg was collected as a colorless liquid which solidified upon cooling. This product analyzed as 98.3 percent 2-chloro-6-(dichloromethyl)pyridine and melted at 50.0°–53.5° C.

EXAMPLE III

A series of runs were conducted following the procedures of Example II employing 0.1 mole of 2-chloro-6-(trichloromethyl)pyridine and 0.2 mole of ferrous chloride as the tetrahydrate and employing different solvents, different amounts of concentrated hydrochloric acid (HCl), varied reaction times and varied reaction temperatures. The results of these runs are set forth below in Table I.

TABLE I

| Run Number | Solvent | Amount of Solvent in grams | Amount of Concentrated HCl in grams | Time in Hours | Temperature | Product analysis *RCHCl$_2$ | *RCH$_2$Cl | *RCCl$_3$ | Unknowns |
|---|---|---|---|---|---|---|---|---|---|
| 1 | None | — | 20 | 2 | 90–120 | 95 | ~2 | Trace | ~3 |
| 2 | Methanol | 10 | 15 | 1.5 | 85 | 86 | Trace | ~5.8 | ~8.2 |
| 3 | n-Butanol | 50 | 10 | 1.5 | 120 | 82 | ~1.2 | ~1.3 | ~15.5 |
| 4 | Isopropanol | 20 | 15 | 3.6 | 85 | 69 | — | ~31 | nil |
| 5 | Acetone | 11 | 11 | 4 | 85 | 91 | — | ~1 | N.D. |

*R = 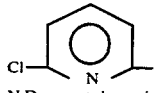

N.D. = not determined

EXAMPLE IV

A series of runs were conducted following the procedures of Example II employing 0.1 mole of 2-chloro-6-(trichloromethyl)pyridine and employing varying amounts of 20-mesh iron fillings, different solvents, different amounts of concentrated hydrochloric acid, varied reaction times and varied reaction temperatures. The results of these runs are set forth below in Table II.

TABLE II

| Run No. | Solvent | Amount of Solvent in grams | Amount of Iron filings in Moles | Amount of Concentrated HCl in grams | Time in Hours | Temp-erature | Product Analysis *RCHCl$_2$ | *RCH$_2$Cl | *RCCl$_3$ | Un-knowns | Comments |
|---|---|---|---|---|---|---|---|---|---|---|---|
| 6 | Methanol | 15 | 0.082 | 15 | 1 | 36 | 94.6 | 3.6 | 1.2 | 0.6 | HCl added over 5 minute period. |
| 7 | Meth- | 15 | 0.032 | 15 | 3 | 36 | 96.6 | ~2.3 | ~1.1 | nil | HCl added over |

TABLE II-continued

| Run No. | Solvent | Amount of Solvent in grams | Amount of Iron filings in Moles | Amount of Concentrated HCl in grams | Time in Hours | Temperature | *RCHCl$_2$ | *RCH$_2$Cl | *RCCl$_3$ | Unknowns | Comments |
|---|---|---|---|---|---|---|---|---|---|---|---|
|  | anol |  |  |  |  |  |  |  |  |  | 5 minute period. Iron added in two portions. |
| 8 | Methanol | 15 | 0.068 | 15 | 1.5 | 85 | 96 | 1.6 | 2.4 | nil | HCl added over 30 minute period. |
| 9 | Methanol | 15 | 0.068 + 0.068 after 1 hour | 15 | 7 | 85 | 91 | — | 2.7 | 6.3 | HCl added dropwise over 25 minutes. |
| 10 | Methanol | 30 | 0.07 | 12 | 4 | 85 | 91.9 | 1.2 | 1.8 | 5.1 | HCl added dropwise over 30 minutes. |
| 11 | Methanol | 15 | 0.068 | 15 | 1.5 | 85 | 90.9 | 2.7 | Trace | 6.4 | ¼ of HCl added over 30 minutes, remainder in 5 minutes. |
| 12 | Methanol | 15 | 0.068 | 15 | 2 | 75 | 9.2 | — | 41.3 | 49.5 | HCl added dropwise over one hour. |
| 13 | None | — | 0.068 | 5 + 26 grams of Acetic Acid | 1.5 | 125 | 82.9 | 14.5 | — | 2.9 | HCl added at once |

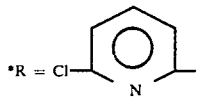

EXAMPLE V:

Preparation of 2-(dichloromethyl)-6-phenoxypyridine

A mixture of 1.0 g (0.0035 mole) of 2-phenoxy-6-(trichloromethyl)pyridine, 2.0 g of methanol and 1.0 g of concentrated hydrochloric acid was heated to 70° C. To this mixture was added 0.16 g (0.0028 mole) of 20 mesh, degreased iron filings, at once. Heating was conducted at mild reflux for 0.5 hour followed by the addition of more iron filing in the amount of 0.06 g (0.0011 mole). After being heated a total of 1.5 hours, the reaction mixture was cooled, diluted with 10.0 g of chloroform and 3 ml of water and filtered to remove insolubles. The filtrate was removed and allowed to separate into aqueous and organic phases with each phase being further extracted with chloroform. The organic layer (phase) was dried over anhydrous sodium sulfate and concentrated under reduced pressure to give 0.71 grams of an amber oil (n$_D^{20}$=1.5902) which was analyzed by glc to be 85.4 percent 2-(dichloromethyl)-6-phenoxypyridine, 11.9 percent 2-(chloromethyl)-6-phenoxypyridine and 2.7 percent unreacted 2-phenoxy-6-(trichloromethyl)pyridine.

What is claimed is:

1. A method for preparing (dichloromethyl) substituted pyridines corresponding to the formula

wherein X represents chloro, bromo, fluoro, aryloxy, alkyl of 1 to 4 carbon atoms, alkoxy of 1 to 4 carbon atoms, alkenyloxy of 2 to 4 carbon atoms, cyano or carboxy; n represents an integer of from 0 to 4 and p is 1 or 2 which comprises reacting the corresponding (trichloromethyl)pyridine compound, under reductive dechlorination conditions, with metallic iron, ferrous chloride or ferrous sulphate and an organic or inorganic acid at temperatures between ~80° and ~120° C.

2. The method as defined by claim 1 wherein the molar equivalent of the metallic iron, ferrous chloride or ferrous sulfate to the pyridine reactant is from ~0.5 to ~3.0 moles of metallic iron, ferrous chloride or ferrous sulfate per trichloromethyl group on the pyridine reactant.

3. The method as defined in claim 2 wherein metallic iron is employed.

4. The method as defined in claim 2 wherein ferrous chloride is employed.

5. The method as defined in claim 1 wherein the (trichloromethyl)pyridine compound is 2-chloro-6-(trichloromethyl)pyridine.

6. The method as defined in claim 1 wherein the (trichloromethyl)pyridine compound is 2-phenoxy-6-(trichloromethyl)pyridine.

* * * * *

UNITED STATES PATENT AND TRADEMARK OFFICE
CERTIFICATE OF CORRECTION

PATENT NO. : 4,260,766
DATED : April 7, 1981
INVENTOR(S) : Leo R. Morris

It is certified that error appears in the above—identified patent and that said Letters Patent is hereby corrected as shown below:

Column 1, line 39, reading "of" should read -- to --.

Column 3 under sub-title Amount of Iron filings in Moles of Table II reading "0.032" should read -- 0.082 --.

Between columns 3 and 4 under sub-title Temperature of Table II in Run No. 6 and 7 reading "36" should read -- 86 --.

Column 4, line 56, reading "fillings" should read -- filings --.

Signed and Sealed this

Thirteenth Day of October 1981

[SEAL]

Attest:

Attesting Officer

GERALD J. MOSSINGHOFF

Commissioner of Patents and Trademarks